(12) United States Patent
Kang (10) Patent No.: US 10,098,579 B2
(45) Date of Patent: Oct. 16, 2018

(54) SYSTEM FOR IMPROVING BRAIN FUNCTION IN ORDER TO PREVENT DEMENTIA AND METHOD FOR OPERATING SAME

(71) Applicant: GAVAPLUS. CO., LTD., Seoul (KR)

(72) Inventor: Young Jin Kang, Gyeonggi-do (KR)

(73) Assignee: GAVAPLUS. CO., LTD., Seoul (KR)

(*) Notice: Subject to any disclaimer, the term of this patent is extended or adjusted under 35 U.S.C. 154(b) by 1086 days.

(21) Appl. No.: 14/373,352

(22) PCT Filed: Jan. 21, 2013

(86) PCT No.: PCT/KR2013/000486
§ 371 (c)(1),
(2) Date: Jul. 19, 2014

(87) PCT Pub. No.: WO2013/109120
PCT Pub. Date: Jul. 25, 2013

(65) Prior Publication Data
US 2015/0010890 A1    Jan. 8, 2015

(30) Foreign Application Priority Data
Jan. 20, 2012  (KR) .................. 10-2012-0006998

(51) Int. Cl.
*G06F 19/00*  (2018.01)
*A61B 5/00*  (2006.01)
(Continued)

(52) U.S. Cl.
CPC .......... *A61B 5/4088* (2013.01); *A61B 5/1112* (2013.01); *G06F 19/3481* (2013.01); *G09B 19/00* (2013.01)

(58) Field of Classification Search
CPC ............. G06F 19/3418; G06F 19/3481; G06F 19/322; G06F 19/325; G06F 19/3406;
(Continued)

(56) References Cited

U.S. PATENT DOCUMENTS

| 8,494,507 B1* | 7/2013 | Tedesco | A61F 4/00 434/112 |
| 2006/0105301 A1* | 5/2006 | Chriss | G06F 19/3418 434/112 |

(Continued)

FOREIGN PATENT DOCUMENTS

| KR | 10-2004-0009045 A | 1/2004 |
| KR | 10-2005-0054379 A | 6/2005 |

(Continued)

OTHER PUBLICATIONS

Grünerbl, Agnes, et al. "Smartphone-based recognition of states and state changes in bipolar disorder patients." IEEE Journal of Biomedical and Health Informatics 19.1 (2015): 140-148.*

(Continued)

*Primary Examiner* — Nathan Hillery
(74) *Attorney, Agent, or Firm* — The PL Law Group, PLLC (57) ABSTRACT

A system for improving brain function includes a brain-function-improving content storage unit that subdivides content for judging the degree of activation of human brain function into multiple classified regions and levels, and stores the subdivided content; a content selection unit that selects the content stored in the brain-function-improving content storage unit for each region according to a predetermined classification method; and an achievement determination unit that determines achievement of a user based on scores acquired through feedback provided by the user for the content selected by the content selection unit. The system may have the effect of protecting subdivided inherent (Continued)

functions of the brain, preventing disorders caused by accidents or diseases, recovering the inherent functions and disorders through analytic diagnosis and repeated study, and training and improving the cognitive ability of significantly impaired portions of brain function by subdividing the inherent functions of the brain.

4 Claims, 3 Drawing Sheets

(51) Int. Cl.
*A61B 5/11* (2006.01)
*G09B 19/00* (2006.01)

(58) Field of Classification Search
CPC ............. G06F 19/3437; G06F 19/3443; G06F 19/345; G06F 19/3456; G06F 19/3487; G06Q 50/22; G06Q 50/24; G09B 19/00; A61B 5/1112; A61B 5/162; A61B 5/165; A61B 5/4088
See application file for complete search history.

(56) References Cited

U.S. PATENT DOCUMENTS

| | | | |
|---|---|---|---|
| 2006/0252014 A1* | 11/2006 | Simon | G09B 23/28 434/236 |
| 2009/0118593 A1* | 5/2009 | Jung | G06Q 50/22 600/300 |
| 2009/0119154 A1* | 5/2009 | Jung | G06Q 30/0204 705/7.33 |
| 2009/0125333 A1* | 5/2009 | Heywood | A61B 5/0002 705/3 |
| 2009/0132275 A1* | 5/2009 | Jung | A61B 5/16 705/2 |
| 2011/0118555 A1* | 5/2011 | Dhumne | A61B 5/16 600/300 |

FOREIGN PATENT DOCUMENTS

| | | |
|---|---|---|
| KR | 10-2008-0084873 A | 9/2008 |
| KR | 10-2009-0067578 A | 6/2009 |

OTHER PUBLICATIONS

International Search Report for PCT/KR2013/000486.

* cited by examiner

SYSTEM FOR IMPROVING BRAIN
FUNCTION IN ORDER TO PREVENT
DEMENTIA AND METHOD FOR
OPERATING SAME

CROSS-REFERENCE TO RELATED
APPLICATION

This patent application claims benefit under 35 U.S.C. 119(e), 120, 121, or 365(c), and is a National Stage entry from International Application No. PCT/KR2013/000486, filed Jan. 21, 2013, which claims priority to Korean Patent Application No. 10-2012-0006998, filed Jan. 20, 2012, the contents of which are hereby incorporated by reference for all purposes as if fully set forth herein.

BACKGROUND

1. Field

The present invention relates to a system for improving brain function in order to prevent dementia, and more particularly, to a system that diagnoses a user's cognitive ability to select learning content, and exercises brain function through the selected content.

2. Description of the Related Art

According to the Diagnostic and Statistical Manual of Mental Disorders (DSM-V) defined by the American Psychiatric Association (APA) for the standard classification of different regions of the brain, brain regions may be mainly classified into the following regions: attention ability, space-time ability, memory, execution ability, language ability, calculation ability, sound recognition ability, and the like.

Dementia defined by the medical community refers to brain diseases that cause a significant reduction in the ability of at least three regions, including the memory region, based on the brain region classification standard.

Recent treatment methods for such dementia include treating or preventing the progress of dementia through drawing pictures to evaluate cognitive ability, puzzle solving provided in the form of games, dialogue, or the like.

These recent treatment methods tend to heavily rely on the judgment of physicians, and therefore, problems associated with the lack of analytical methods for evaluating the cognitive ability of patients with dementia have been noted.

In addition, various treatment methods for patients with dementia are performed via human dialogue, and therefore, similar problems associated with the lack of analytical metrics to track treatment progress or results have been noted. Lastly, even good preventative programs lack preventative effects for dementia because deterioration of the effects occurs when learning is not periodically maintained.

SUMMARY

The present invention is directed to providing a system that classifies the cognitive ability of patients with dementia via subdivided criteria to diagnose the progress of dementia, and outputs content for improving brain function suitable for the degree of progress of dementia to obtain diagnostic results based on the output values.

Further, the present invention is directed to providing a system by which dementia is prevented by periodically executing a preventive program for dementia, and notifying caregivers of patients whether the preventive program for dementia is executed.

Yet further still, the present invention is directed to providing a system that indirectly notifies caregivers of the conditions of elderly people by notifying the caregivers whether a periodic preventive program for dementia is executed.

One aspect of the present invention provides a system for improving brain function in order to prevent dementia, including: a brain-function-improving content storage unit that subdivides content for judging the degree of activation of human brain function into multiple classified regions and levels and stores the subdivided content; a content selection unit that selects the content stored in the brain-function-improving content storage unit for each region according to a predetermined classification method; and an achievement determination unit that determines achievement of a user based on scores acquired through feedback provided by the user for the content selected by the content selection unit.

Here, the content selection unit may convert the content into a score via a weight for each level, and select the content so that a sum of the scores in which the weight is reflected for each region is constant.

Also, the content selection unit may select the content of a predetermined level or greater according to the achievement of the user determined by the achievement determination unit.

Further, the system may include a content change adjustment unit that controls the content selection unit to newly adjust and select the level when feedback including consecutive correct answers or incorrect answers to at least two items of the selected content, is transmitted by the user.

Further still, the system may include a diagnosis result calculation unit that schematizes the achievement of the user according to the classified regions based on a predetermined classification standard; and a diagnosis result storage unit that classifies and stores the achievement of the user for each region and for each period of time.

Yet further still, the content selection unit may select the content based on the region and the level that is manually assigned by the user.

The system may further include a user information storage unit that inputs personal information of a plurality of users, assigns unique identification text to each user, associates diagnosed achievement information with each user, and stores the associated information.

Further, the system may include a sleep mode determination unit that determines, as a sleep mode, a case in which a specific time is set according to a predetermined period of time and the system for improving brain function is not used by the user after the predetermined period of time; a message generating unit that generates a message for notifying a caregiver of the user in sleep mode; a Global Positioning System (GPS) unit that generates current position information of the user in sleep mode; and a communication unit that transmits the message and the current position information of the user to the caregiver of the user.

Further still, the system may include an alarm unit that includes at least one of a lighting device, an audio device, and a vibration device; and a mobile device that is separated from the system for improving brain function and is linked to the communication unit. Here, the alarm unit may generate an alarm when the mobile device is separated from the system for improving brain function by a certain distance or greater, and when the mobile device does not periodically communicate with the communication unit.

Another aspect of the present invention provides a method of operating a system for improving brain function in order to prevent dementia, including: registering a user in the system by providing the personal information of the user; selecting content for judging the degree of activation of human brain function stored for each of the multiple regions and levels by a predetermined standard, and submitting the selected content to the user; inputting feedback to the submitted content by the user; determining achievement based on the scores acquired through the feedback; and changing and selecting the level of the content for each region according to the predetermined standard by reflecting the achievement, and submitting the changed and selected level of the content to the user.

Yet another aspect of the present invention provides a method of operating a system for improving brain function in order to prevent dementia, including: selecting content for judging the degree of activation of human brain function stored for each of the multiple regions and levels by a predetermined standard, and submitting the selected content to the user; inputting feedback to the submitted content by the user; calculating the percentage of correct answers of the user according to the feedback; and selecting the content of a changed level when the percentage of correct answers is greater or less than a predetermined standard, and submitting the selected content to the user.

Yet still another aspect of the present invention provides a method of operating a system for improving brain function in order to prevent dementia, including: determining whether a specific time is set according to a predetermined period of time and the system for improving brain function is used by a user at the specific time according to the predetermined period of time; generating current position information of the user and a message for notifying a caregiver of the user when the system for improving brain function is not being used by the user at the specific time according to the predetermined period of time; and transmitting the current position information of the user and the message to the caregiver.

According to the present invention, the system for improving brain function in order to prevent dementia may have the effects of protecting subdivided inherent functions of the brain, preventing disorders caused by accidents or diseases, and recovering the inherent functions and disorders through analytic diagnosis and repeated study.

In addition, the system for improving brain function in order to prevent dementia may have the effects of training and improving the cognitive ability of a significantly impaired part of brain function by subdividing the inherent function of the brain.

Further, when the system for improving brain function is set to be periodically executed and yet is not executed within a set period of time, the system may be periodically executed by notifying the caregivers of the patients that the system has not been executed.

Further still, when the system for improving brain function is not executed for a long period of time, the caregivers of patients, or an emergency center, may be informed of the personal status of the user by being notified that the system has not been executed.

Yet further still, the communication settings between the user and the system for improving brain function may be adjusted, and therefore, an alarm may be generated when the system is separated from the user by a certain distance or greater, thereby preventing loss of the system.

DETAILED DESCRIPTION

Hereinafter, preferred embodiments of the present disclosure will be described in detail with reference to the accompanying drawings. Terms used in the specification and the appended claims should not be construed as limited to their general dictionary meanings, but interpreted based on the meanings and concepts corresponding to technical aspects of the present disclosure and based on the principle that the inventor is allowed to define terms accordingly for the best explanation. Therefore, the description proposed herein is merely exemplary and for the purposes of illustration only, and is not intended to limit the scope of the disclosure, thus it should be understood that other equivalents and modifications could be made thereto without departing from the spirit and scope of the disclosure.

Figure 1:
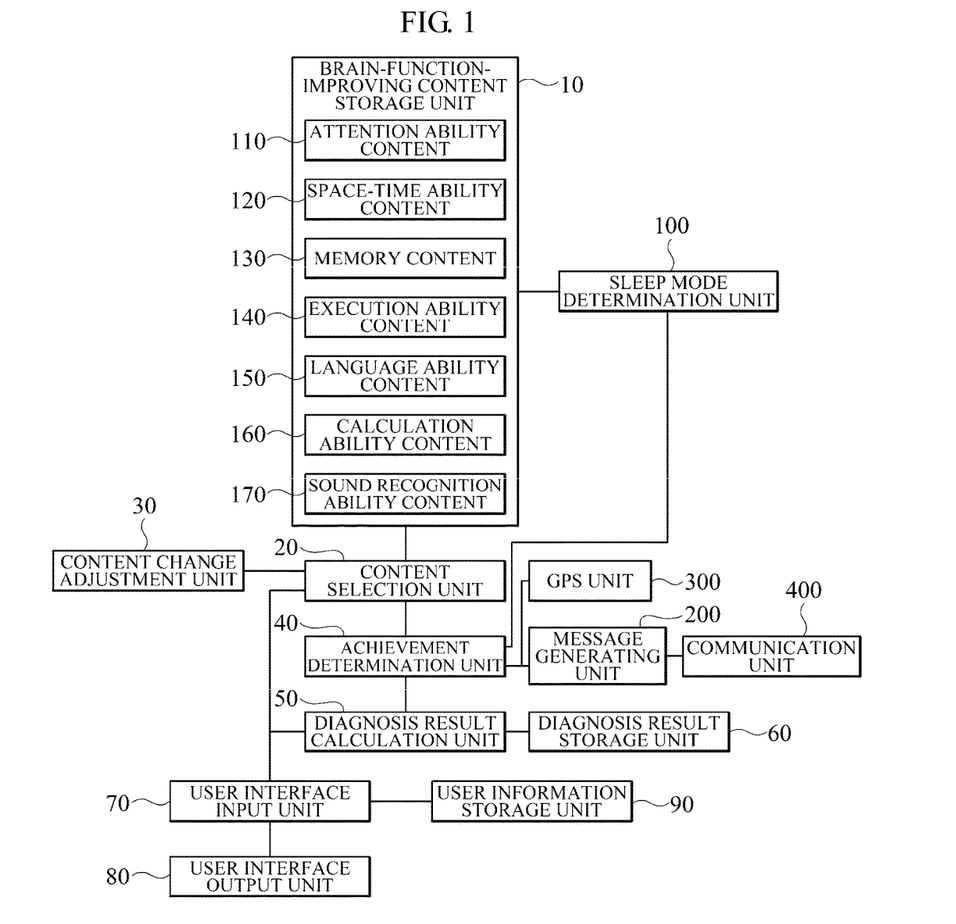
FIG. 1 is a diagram illustrating a configuration of a system for improving brain function in order to prevent dementia according to an embodiment of the present invention.
Figure 2:
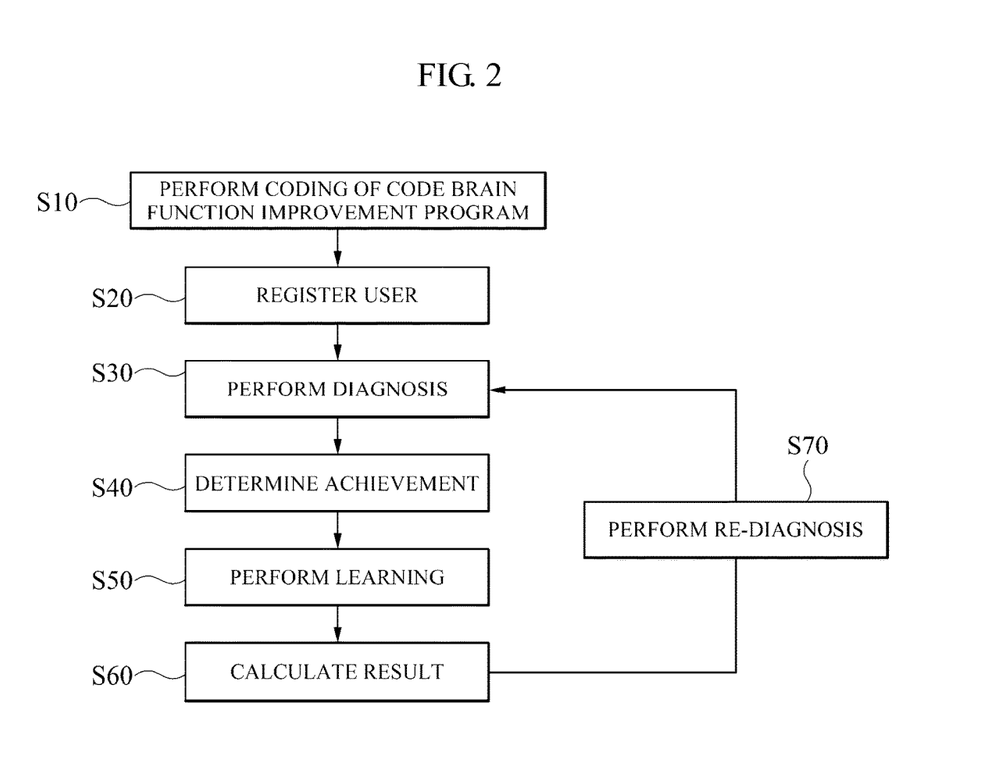
FIG. 2 is a flowchart illustrating a method of operating a system for improving brain function in order to prevent dementia according to an embodiment of the present invention.

FIG. 1 is a diagram illustrating a configuration of a system for improving brain function in order to prevent dementia according to an embodiment of the present invention, and FIG. 2 is a flowchart illustrating a method of operating a system for improving brain function in order to prevent dementia according to an embodiment of the present invention.

The system for improving brain function in order to prevent dementia according to an embodiment of the present invention includes a brain-function-improving content storage unit 10, a content selection unit 20, a content change adjustment unit 30, an achievement determination unit 40, a diagnosis result calculation unit 50, a diagnosis result storage unit 60, a user interface input unit 70, a user interface output unit 80, a user information storage unit 90, a sleep mode determination unit 100, a message generating unit 200, a Global Positioning System (GPS) unit 300, and a communication unit 400. Here, although not shown, the system may further include an alarm unit.

In addition, a user may carry a mobile device linked to the system for improving brain function.

In operation S10 (FIG. 2), in order to determine the degree of activation of brain function of a user and diagnose dementia or dementia-related diseases, a program for the system for improving brain function may be loaded.

Next, in operation S20, when information needed for registration of user information is determined through the user interface output unit 80, the user information may be provided through the user interface input unit 70 in order to register a user.

The user interface input unit 70 may include various mechanisms for computerizing feedback information, including text or voice information transmitted to the system by the user, and inputs the computerized information as electrical signals via mechanisms such as a keyboard, a mouse, a microphone, and the like.

The user interface output unit 80 may output information transmitted to the user from the system, or information input by the user. The user interface output unit 80 may include various output mechanisms including a monitor for the display of information, and a speaker for voice output.

The user information that is input by the user in order to register the user may be stored in the user information storage unit 90. Thus, the user information storage unit 90 may assign unique identification text to the registered user, and associate achievement information, obtained in the diagnosis and training process of the user, with each identification text to thereby store the associated information.

Next, the system for improving brain function according to an embodiment of the present invention may select content for judging the degree of activation of human brain function stored for each of the multiple regions and levels by a predetermined standard, and submit the selected content to the user. Thus, in operation S30, the user may input feedback information with respect to the selected content through the user interface input unit 70.

The content selection unit 20 may select the content of seven human brain function regions stored in the brain-function-improving content storage unit 10 according to a predetermined classification method, and submit the selected content to the user interface output unit 80.

The brain-function-improving content storage unit 10 may classify content and store the classified content into attention ability content 110, space-time ability content 120, memory content 130, execution ability content 140, language ability content 150, calculation ability content 160, and sound recognition ability content 170.

The attention ability content 110 may include content associated with finding the same picture or evaluating attentiveness to text.

The space-time ability content 120 may include content associated with evaluating the perception of objects or visual association.

The memory content 130 may include content associated with remembering flags, cards, or numbers.

The execution ability content 140 may include content associated with evaluating picture completion, categorization ability, or similarity assessability.

The language ability content 150 may include content associated with evaluating word completion or word location.

The calculation ability content 160 may include content associated with evaluating calculations through the four arithmetical operations.

The sound recognition ability content 170 may include content associated with finding a picture that matches a sound, or finding pictures according to an order in which sounds were heard.

The content selection unit 20 may select content of a different level according to whether a user to be diagnosed is a normal person, an elderly person, a person with dementia, or a person belonging to a dementia high-risk group, among the content of seven brain function regions included in the brain-function-improving content storage unit 10.

The content selection unit 20 may select the content in such a manner that 100 points are completed by assigning a weight to a problem according to each level based on a total score of 100 points for each region. For example, the level interval of the attention ability content 110 may constitute levels 1 to 5, and 100 problems may be selected from the content of level 1, 50 problems may be selected from the content of level 2, or 20 problems may be selected from the content of level 5.

Next, in operation S40, whether or not the content has been answered correctly is determined, using the feedback information provided by the user in operation S30, to calculate the acquired score, and the achievement according to the calculated score is determined The achievement determination unit 40 may assign the achievement depending on the achievement rating that is set by a plurality of intervals based on the acquired scores. For example, based on the acquired score of the user, an A rating may be assigned in the case of a perfect score to 66 points, a B rating may be assigned in the case of 65 to 34 points, and a C rating may be assigned in the case of 33 to 0 points.

Here, the achievement determination unit 40 may be connected to the sleep mode determination unit 100, the message generating unit 200, the GPS unit 300, and the communication unit 400, and therefore, when a user does not use the system for improving brain function for a predetermined period of time, a message and current position information may be respectively generated in the message generating unit 200 and the GPS unit 300.

In addition, the achievement determination unit 40 may transmit an emergency message, including the generated message and current position information, to the caregiver of the user through the communication unit 400.

Next, in operation S50, the level of the content is changed and selected for each region based on the predetermined standard according to the achievement rating assigned to the user in operation S40, and the changed and selected level of the content is submitted to the user to perform learning.

The content selection unit 20 may select the level of the content submitted according to the achievement of the user assigned in the achievement determination unit 40 as content of a predetermined level or greater.

For example, the achievement of an A rating is classified as early cognitive impairment or the level of a normal person, and thus selection starts from the content of level 3. The achievement of a B rating is classified as slight cognitive impairment or an older age group, and thus selection starts from the content of level 2. The achievement of a C rating is classified as dementia or a dementia high-risk group, and thus selection starts from the content of level 1.

Next, in operation S60, the achievement of the user may be schematized according to a predetermined classification standard for each region of the cognitive ability to calculate results for diagnosis and learning.

The diagnosis result calculation unit 50 may schematize the score acquired in a process in which a user solves the selected content within units of certain periods of time, and the achievement according to the acquired score.

As a method of schematizing the score and the achievement, the results are represented in the form of graphs including a bar graph, a curved graph, a line graph, and the like, and the acquired score and the achievement rating may be written as text.

The diagnosis result storage unit 60 may classify and store diagnostic result data obtained in the diagnosis result calculation unit 50 for each region of the cognitive ability, and for each period of time. Next, in operation S70, when a certain period of time passes, re-diagnosis may be performed to re-check the progress of the cognitive ability of the user.

The sleep mode determination unit 100 determines whether the user periodically executes the program for improving brain function using the system for improving brain function. For this, the sleep mode determination unit 100 may set a time at which a user should periodically use the system for improving brain function.

For example, when setting a time wherein a user should use the system for improving brain function at 10:00 am every 24 hours, the sleep mode determination unit 100 determines whether the system for improving brain function is operated at the corresponding time for each corresponding time cycle. That is, a determination is made whether or not a user uses the system for improving brain function at 10:00 am every day. When the user does not use the system for improving brain function at the corresponding time according to the predetermined period of time, it is determined that an emergency situation has occurred, and thus a signal for generating a current position of the user (i.e., a position of the system for improving brain function) and a signal for generating an emergency situation message are generated.

Here, the emergency situation message may be transmitted to the caregiver of the user or a public office near the user's home.

The message generating unit 200 generates an emergency message including the fact that the user is in an emergency situation upon receiving the message generating signal from the sleep mode determination unit 100. Here, the message may be a short message service (SMS) or multimedia messaging service (MMS) message.

Here, the message generating unit 200 may receive the current position information of the user from the GPS unit 300, and generate a message including the position information of the user by enabling the received information to be included in the emergency message.

Upon receiving the signal for generating the current position of the user from the sleep mode determination unit 100, the GPS unit 300 is activated to generate the current position information of the user.

Here, the user position denotes a position of the system for improving brain function, and the generated current position information of the user may be GPS coordinates or address information.

The GPS unit 300 transmits the generated current position of the user to the message generating unit 200.

The functions of the communication unit 400 may be performed using WIFI or mobile communication, such as 3G or 4G. In addition, the communication unit 400 may perform short-range wireless communication, such as Bluetooth, Zigbee, or near field communication (NFC).

The communication unit 400 may transmit the emergency message generated in the system for improving brain function to the caregiver of the user.

Here, when the user who carries a device linked to the communication unit 400 is separated from the system for improving brain function by a predetermined distance or greater, and/or communication between the device carried by the user and the system for improving brain function is cut off, the communication unit 400 may generate an alarm signal and transmit the generated alarm signal to an alarm device (not illustrated) of the system for improving brain function, thereby sounding an alarm.

Here, the device that is carried by the user and is linked to the communication unit 400 may be provided in the form of a necklace, a bracelet, an anklet, or a belt that the user may be carrying.

Additionally, in the system for improving brain function, identification information of the system is included in the user information storage unit 90, and therefore, the communication unit 400 may receive the identification information of the system from a remote communication device to generate an alarm signal. In this case, the system for improving brain function may register the identification information in a mobile communication network or an Access Point (AP).

For example, when a user makes a call through a mobile phone using the identification information of the corresponding system, the system for improving brain function sounds the alarm. Alternatively, the alarm of the system may be triggered, and the current position of the system for improving brain function obtained when the user accesses an address corresponding to the identification information of the system through the AP.

Here, the emergency message may be generated in the system for improving brain function itself, and when the system is linked to a message server in a communication network, the emergency message stored in the message server may be transmitted to the caregiver of the user by transmitting a message generating signal—which may include position information—to the message server of the communication network.

Here, the system for improving brain function may perform a call directly with the caregiver of the user through the communication unit 400.

For example, when the user does not use the system for improving brain function at the time set in the sleep mode determination unit 100, the emergency message may be transmitted to the caregiver of the user, and the caregiver of the user may connect a call with the system for improving brain function through a mobile communication network to thereby perform a call with the user.

Here, when the user does not receive the call, it is determined that a problem has occurred with the user, and connection with a public office, such as a police station or an emergency center near the user's home, is automatically performed to provide care services to the user.

In the present invention, the system for improving brain function may be a terminal, such as a computer, connected to the Internet, or a mobile terminal that can be carried by the user.

Figure 3:
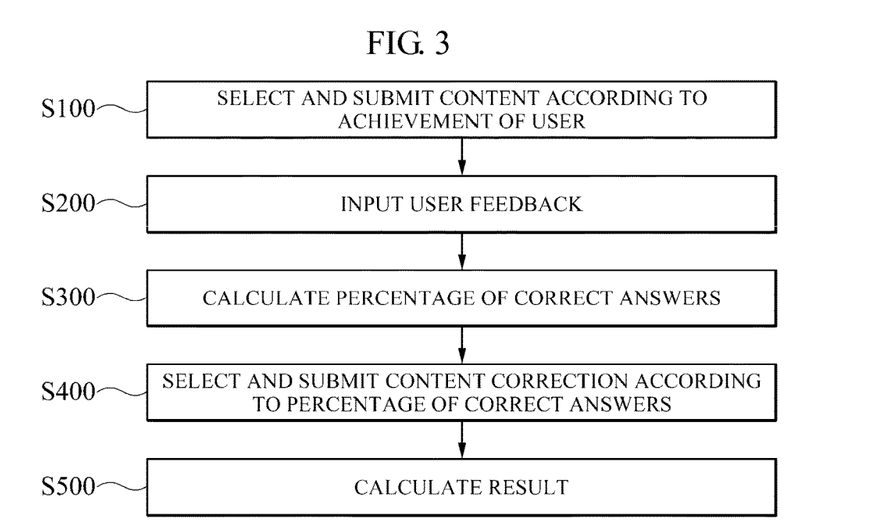
FIG. 3 is a flowchart illustrating a method of operating a system for improving brain function in order to prevent dementia according to another embodiment of the present invention.

FIG. 3 is a flowchart illustrating a method of operating a system for improving brain function in order to prevent dementia according to another embodiment of the present invention.

The operations S100, for selecting and submitting content according to the achievement of the user, and S200, for inputting feedback of the user, are the same as the learning operation S50 described in FIG. 2, and thus a detailed description thereof will be omitted.

Next, the user may input feedback information in operation S200, and the percentage of correct answers may be calculated according to the feedback information of the user in operation S300.

Next, in operation S400, the corrected content may be selected and submitted by changing the standard of selecting the content according to the percentage of correct answers calculated in operation S300.

The content change adjustment unit 30 may analyze the percentage of correct answers based on the feedback information of the user, and control the content selection unit 20 to newly adjust and select the level when at least two consecutive items of the selected content are answered correctly or incorrectly. For example, in a process in which the user acquires the achievement of a B rating in the attention ability region and the content of level 2 or higher is selected and submitted to perform learning, when the user consecutively answers three items of content correctly, the selection standard may be changed, such as selecting the content of level 3 or higher in the attention ability region.

In contrast, when the user consecutively answers two items of content incorrectly, the selection standard may be changed, such as selecting the content of level 1 or higher in the attention ability region.

Operation S500 is the same as operation S60 described in FIG. 2, and thus a detailed description thereof will be omitted.

Figure 4:
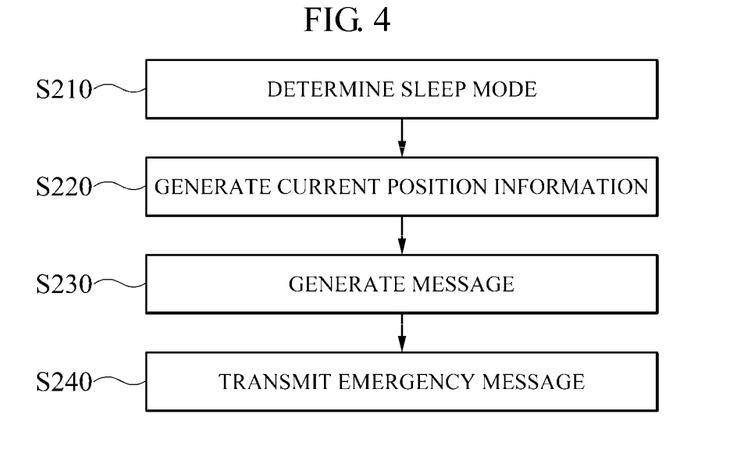
FIG. 4 is a flowchart illustrating a method of operating a system for improving brain function according to yet another embodiment of the present invention.

FIG. 4 is a flowchart illustrating a method of operating a system for improving brain function according to another embodiment of the present invention.

In operation S210, it is determined whether or not the system for improving brain function is in a sleep mode.

Here, the sleep mode may indicate a case in which a user does not use the system for improving brain function at a set time according to a set period of time, and therefore, the system is not operated for the set period of time or longer.

As described above, in operation S210, when a time at which a user periodically uses the system for improving brain function is set, it is determined whether the user uses the system at the set time according to the set period of time.

In operation S220, when the user does not use the system at the set time according to the set period of time, current position information of the user is generated. The current position information of the user is generated through the GPS unit 300, as described above. Alternatively, when the system for improving brain function is linked to a mobile communication network, the current position information of the user is generated through a Location Based Server (LBS) using base station information.

In operation S230, the message generating unit 200 generates an SMS or MMS message.

In operation S240, an emergency message, including the generated current position information of the user and the generated SMS or MMS message, is generated to be transmitted to the caregiver of the user, a public office near the user's home, or a care facility taking care of the user.

The system for improving brain function according to the present invention may be more commonly used by elderly people. In particular, when the system is used by elderly people who live alone, an emergency message received from the system can be assumed to mean that a problem has occurred with the user.

Thus, in this case, it should be determined whether or not a problem has occurred with the user by immediately finding the user.

A method in which the brain function improving content 110 to 170 is classified as seven regions to analytically diagnose a user is theoretically based on Hofmann M, Hock C, Kuhler A, Muller-Spahn F. Interactive computer-based cognitive training in patients with Alzheimer's disease. J Psychiatr Res 1996;30:493-501, and Flynn D, van Schaik P, Blackman T, Femcott C, Hobbs B, Calderon C. Developing a virtual reality-based methodology for people with dementia: a feasibility study. Cyberpsychol Behav 2003; 6:591-611.

In the study of Hoffman and the like reported in 1996 among studies on dementia using a computer, a system in which 10 patients with dementia received stimuli through a touch screen while being shown 50 to 150 photos that the 10 patients with dementia were familiar with according to the scenario for cognitive rehabilitation was configured. It was reported that the performance of the patients with dementia improved after training for three weeks. In addition, when a virtual reality having a park as the background was shown to 6 patients with dementia in the studies of Flynn and the like, it was reported that the 6 patients with dementia moved naturally using a joystick while feeling a sense of reality with respect to the virtual reality without any particular side effects. That is, this can be evaluated as suggesting that there is a basis for using virtual reality technology in cognitive function evaluation or cognitive rehabilitation by applying the virtual reality technology to patients with dementia.

Thus, the system for improving brain function according to the prevent invention has theoretical support based on the above-described theses, and has effects of preventing and alleviating dementia diseases according to degradation in cognitive ability.

Although exemplary embodiments of the present invention have been described as first, second, and third exemplary embodiments for conciseness, the respective steps or functions of any exemplary embodiment may be combined with those of any other exemplary embodiment to implement still another exemplary embodiment of the present invention. While the invention has been described with reference to certain exemplary embodiments thereof, it will be understood by those skilled in the art that various changes in the form and details of the invention may be made without departing from the spirit and scope of the invention as defined by the appended claims.

The invention claimed is:

1. A system for improving brain function in order to prevent dementia, the system comprising:
   a user interface input unit to input a user's information to register a user;
   a user interface output unit to output information transmitted to the user from the system, or information input by the user;
   a user information storage unit in which the user's information input that is inputted via the user interface input unit is stored, the user information storage unit that assigns unique identification text to the user, and associate diagnosed achievement information with each identification text to thereby store associated information, the user information storage unit including identification information of the system;
   a brain-function-improving content storage unit, executed by a computer or a mobile terminal, that subdivides content for judging a degree of activation of human brain function into multiple classified regions and levels and stores the subdivided content;
   a content selection unit executed by the computer or the mobile terminal, the content selection unit that selects a content from the content stored in the brain-function-improving content storage unit for each region according to a predetermined classification method, and submits the selected content to the user interface output unit, the content selection unit that converts the content into a score by a weight for each level, and selects the content so that a sum of the scores in which the weight is reflected for each region is constant;
   an achievement determination unit executed by the computer or the mobile terminal, the achievement determination unit that determines achievement of the user based on scores acquired through feedback provided by the user for the content selected by the content selection unit; and
   a content change adjustment unit executed by the computer or the mobile terminal, the content change adjustment unit that controls the content selection unit to newly adjust and select the level when feedback including consecutive correct answers or incorrect answers to at least two items of the selected content is transmitted by the user;
   an alarm unit that includes at least one of a lighting device, an audio device, and a vibration device; and
   a sleep mode determination unit executed by the computer or the mobile terminal, the sleep mode determination unit that determines, as a sleep mode, a case in which a specific time is set according to a predetermined period of time and the system is not used by the user after the predetermined period of time;

a Global Positioning System (GPS) unit executed by the computer or the mobile terminal, the Global Positioning System (GPS) unit that generates current position information of the user in the case of the sleep mode, and transmits the generated current position of the user;

a message generating unit executed by the computer or the mobile terminal, the message generating unit that receives the current position information of the user from the GPS unit, and generates a message with the position information of the user for notifying a caregiver of the user in a case of the sleep mode;

a communication unit executed by the computer or the mobile terminal, the communication unit that transmits the message and the current position information to the caregiver of the user; and a mobile device that is separated from the computer or the mobile terminal and is linked to the communication unit;

wherein the system registers the identification information in a mobile communication network or an Access Point (AP), and, when the user who carries the mobile device is separated from the system by a predetermined distance or greater, or communication between the mobile device and the system is cut off, the communication unit that receives the identification information of the system from the mobile communication network or the Access Point generates an alarm signal and transmit the generated alarm signal to the alarm device of the system.

2. The system of claim 1, wherein the content selection unit selects the content of a predetermined level or greater according to the achievement of the user determined by the achievement determination unit.

3. The system of claim 1, further comprising:
a diagnosis result calculation unit executed by the computer or the mobile terminal, the diagnosis result consultation unit that schematizes the achievement of the user according to the classified regions based on a predetermined classification standard; and
a diagnosis result storage unit executed by the computer or the mobile terminal, the diagnosis result storage that classifies and stores the achievement of the user for each region and for each period of time.

4. The system of claim 1, wherein the content selection unit selects the content based on the region and the level that are manually assigned by the user.

* * * * *